(12) United States Patent
Duffy et al.

(10) Patent No.: US 11,141,572 B2
(45) Date of Patent: Oct. 12, 2021

(54) CONTROL MODULE FOR DELIVERY SYSTEMS

(71) Applicant: Medtronic Vascular Galway, Ballybrit (IE)

(72) Inventors: Niall Duffy, Ballybrit (IE); John Gallagher, Ballybrit (IE); Gerry McCaffrey, Ballybrit (IE)

(73) Assignee: Medtronic Vascular Galway, Ballybrit (IE)

(*) Notice: Subject to any disclaimer, the term of this patent is extended or adjusted under 35 U.S.C. 154(b) by 378 days.

(21) Appl. No.: 16/225,545

(22) Filed: Dec. 19, 2018

(65) Prior Publication Data
US 2019/0117940 A1    Apr. 25, 2019

Related U.S. Application Data

(63) Continuation of application No. 14/686,159, filed on Apr. 14, 2015, now Pat. No. 10,159,819.

(60) Provisional application No. 61/983,560, filed on Apr. 24, 2014, provisional application No. 62/048,929, filed on Sep. 11, 2014.

(51) Int. Cl.
*A61M 25/09* (2006.01)
*A61F 2/95* (2013.01)
*A61F 2/966* (2013.01)

(52) U.S. Cl.
CPC ......... *A61M 25/09041* (2013.01); *A61F 2/95* (2013.01); *A61F 2/966* (2013.01); *A61F 2/9517* (2020.05); *A61M 2025/09125* (2013.01)

(58) Field of Classification Search
CPC ... A61M 25/09041; A61M 2025/09125; A61F 2/95; A61F 2/966; A61F 2002/9517
See application file for complete search history.

(56) References Cited

U.S. PATENT DOCUMENTS

| | | | | |
|---|---|---|---|---|
| 3,312,128 A | * | 4/1967 | Wasson ................. | E04G 21/122 81/487 |
| 4,844,092 A | * | 7/1989 | Rydell .................. | A61M 25/01 600/585 |
| 4,932,959 A | * | 6/1990 | Horzewski ............ | A61M 25/01 604/96.01 |
| 5,035,705 A | * | 7/1991 | Burns ................ | A61M 25/0075 606/194 |
| 5,045,061 A | * | 9/1991 | Seifert .................. | A61M 25/09 604/96.01 |
| 5,085,636 A | * | 2/1992 | Burns ................ | A61M 25/0075 604/913 |
| 5,217,434 A | * | 6/1993 | Arney ................ | A61M 25/0054 604/103.1 |
| 5,221,260 A | * | 6/1993 | Burns ................ | A61M 25/0075 604/913 |
| 5,325,746 A | * | 7/1994 | Anderson ............... | A61B 17/22 24/115 M |
| 5,327,906 A | * | 7/1994 | Fideler .............. | A61M 25/0136 600/585 |

(Continued)

*Primary Examiner* — Phong Son H Dang
(74) *Attorney, Agent, or Firm* — Dicke, Billig & Czaja, PLLC

(57) ABSTRACT

A guidewire is coupled to a control module and extends through a lumen of the control module. The control module operates to transition between a first control state wherein the control module allows movement of the guidewire relative to a catheter and a second control state wherein relative axial movement between the catheter and guidewire is prevented.

12 Claims, 8 Drawing Sheets

(56) References Cited

U.S. PATENT DOCUMENTS

| | | | | |
|---|---|---|---|---|
| 5,346,498 | A * | 9/1994 | Greelis | A61M 25/0119 604/271 |
| 5,360,403 | A * | 11/1994 | Mische | A61M 25/0075 604/101.02 |
| 5,454,789 | A * | 10/1995 | Burns | A61M 25/0075 604/99.04 |
| 5,919,161 | A * | 7/1999 | Hill, III | A61M 25/09041 604/95.01 |
| 6,010,464 | A * | 1/2000 | Galdonik | A61M 25/0169 600/585 |
| 6,059,739 | A * | 5/2000 | Baumann | A61M 25/0147 600/585 |
| 6,117,140 | A * | 9/2000 | Munsinger | A61F 2/95 606/108 |
| 6,149,663 | A * | 11/2000 | Strandberg | A61B 17/320758 600/581 |
| 6,231,543 | B1 * | 5/2001 | Hegde | A61M 25/10 604/96.01 |
| 6,485,466 | B2 * | 11/2002 | Hamilton | A61M 25/0113 600/585 |
| 6,752,800 | B1 * | 6/2004 | Winston | A61M 25/09041 604/157 |
| 6,827,718 | B2 | 12/2004 | Hutchins et al. | |
| 7,637,863 | B2 * | 12/2009 | Deal | A61B 1/012 600/104 |
| 7,674,282 | B2 * | 3/2010 | Wu | A61F 2/966 623/1.11 |
| 7,794,487 | B2 * | 9/2010 | Majercak | A61F 2/95 623/1.11 |
| 7,914,569 | B2 | 3/2011 | Nguyen et al. | |
| 7,993,392 | B2 * | 8/2011 | Righini | A61F 2/2436 623/2.11 |
| 8,016,877 | B2 | 9/2011 | Seguin et al. | |
| 8,562,568 | B2 * | 10/2013 | Datta | A61M 25/09041 604/165.04 |
| 8,992,480 | B2 * | 3/2015 | Gallacher | A61M 25/0169 604/164.13 |
| 9,271,856 | B2 * | 3/2016 | Duffy | A61F 2/966 |
| 9,615,951 | B2 * | 4/2017 | Bennett | A61F 2/95 |
| 10,118,025 | B2 * | 11/2018 | Doi | A61M 25/10 |
| 2007/0239159 | A1 * | 10/2007 | Altarac | A61B 17/7014 606/86 A |
| 2007/0270755 | A1 * | 11/2007 | Von Oepen | B25B 9/00 604/164.13 |
| 2008/0114390 | A1 * | 5/2008 | Guinan | A61M 25/09041 606/194 |
| 2009/0228093 | A1 | 9/2009 | Taylor et al. | |
| 2009/0287188 | A1 * | 11/2009 | Golden | A61M 25/0147 604/528 |
| 2010/0069833 | A1 * | 3/2010 | Wenderow | A61B 90/98 604/95.01 |
| 2010/0125244 | A1 * | 5/2010 | McAndrew | A61M 25/10 604/98.01 |
| 2010/0204613 | A1 * | 8/2010 | Rollins | A61B 17/320758 600/585 |
| 2012/0239142 | A1 | 9/2012 | Liu et al. | |
| 2012/0245490 | A1 * | 9/2012 | Fausett | A61B 5/4362 600/595 |
| 2012/0271339 | A1 * | 10/2012 | O'Beirne | A61M 25/104 606/194 |
| 2013/0281787 | A1 * | 10/2013 | Avneri | A61M 25/0133 600/208 |
| 2014/0187984 | A1 * | 7/2014 | Burkett | A61B 5/0215 600/486 |
| 2014/0324026 | A1 * | 10/2014 | Chrisman | A61M 25/09041 604/528 |
| 2015/0231364 | A1 * | 8/2015 | Blanchard | A61M 25/09041 604/164.08 |
| 2016/0256667 | A1 * | 9/2016 | Ribelin | A61M 25/0618 |

* cited by examiner

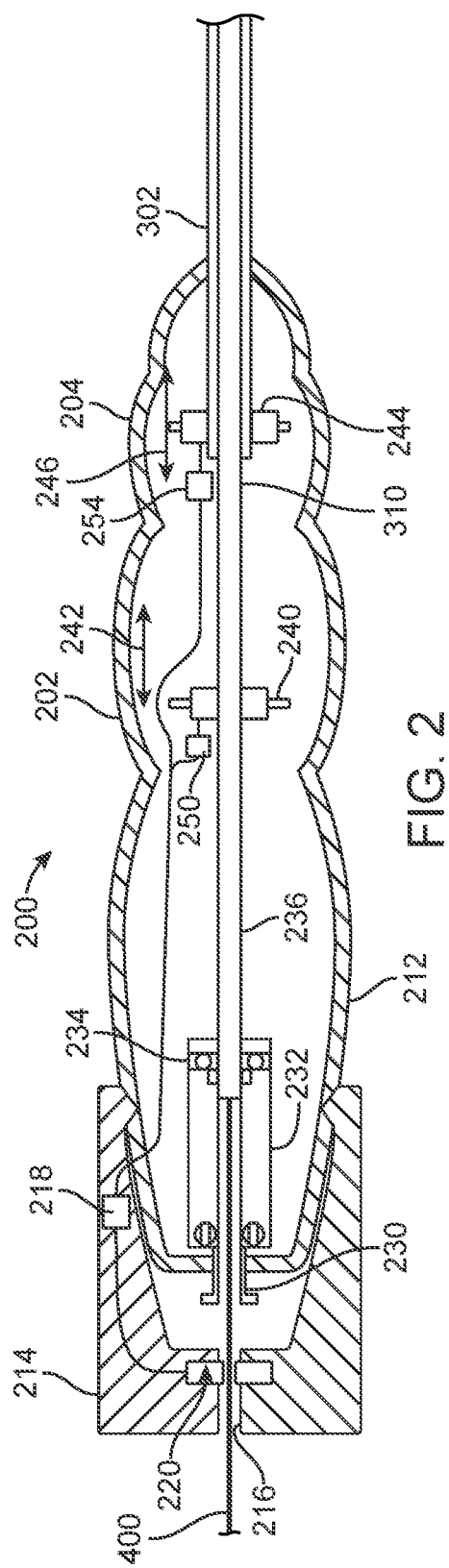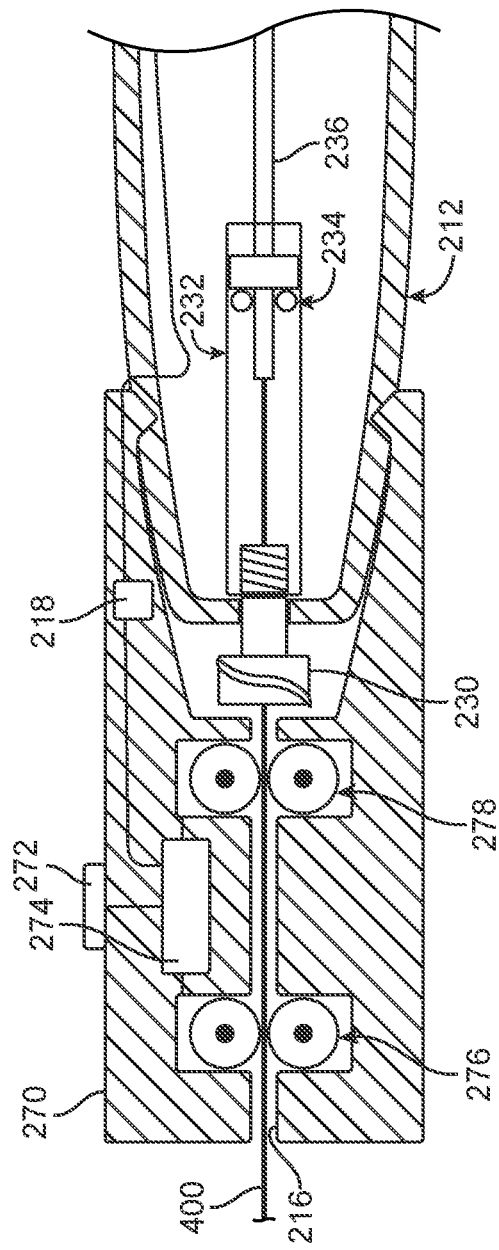
FIG. 2
FIG. 3

CONTROL MODULE FOR DELIVERY SYSTEMS

CROSS REFERENCE TO RELATED APPLICATIONS

This application is a continuation application of Ser. No. 14/686,159, filed Apr. 14, 2015 which is a non-provisional application of 62/048,929, filed on Sep. 11, 2014, entitled "CONTROL MODULE FOR DELIVERY SYSTEM," and of U.S. Patent Application Ser. No. 61/983,560, filed on Apr. 24, 2014, entitled "CONTROL MODULE FOR DELIVERY SYSTEMS," wherein all of these applications are assigned to the assignee of the present application and the entire contents of all of these applications are incorporated herein by reference.

BACKGROUND

Currently, replacement of a deficient cardiac valve is often performed by placing the patient under extracorporeal circulation, temporarily stopping the heart, opening the thorax (e.g., by a sternotomy), surgically opening the heart, excising the deficient valve, and then implanting a prosthetic valve in its place. This procedure generally requires prolonged patient hospitalization, as well as extensive and often painful recovery.

Recently, minimally invasive approaches have been developed to facilitate catheter-based implantation of valve prostheses in the beating heart, intending to obviate the need for the classic sternotomy and cardiopulmonary bypass. For example, U.S. Pat. No. 8,016,877 to Seguin et al. illustrates a technique and a device for replacing a deficient heart valve by percutaneous route. An expandable prosthetic valve can be compressed about a catheter, inserted inside a body lumen, such as the femoral artery, and delivered to a desired location in the heart. Additionally, U.S. Pat. No. 7,914,569 to Nguyen et al. discloses advancing a catheter containing a prosthesis in a retrograde manner through the femoral artery and into the descending aorta, over the aortic arch, through the ascending aorta and inside the defective aortic valve. This procedure can be assisted by fluoroscopic guidance. Once the position of the catheter containing the prosthesis is confirmed, a sheath containing the prosthesis can be moved proximally, allowing the valve prosthesis to self-expand.

In some current approaches, a guidewire is utilized to guide the catheter during delivery. The guidewire can be routed through a patient's vasculature to the desired location. Once the guidewire is in place, the catheter is advanced over the guidewire so as to deploy the prosthesis. During advancement of the catheter and deployment of the prosthesis, management of the guidewire is important so as to prevent inadvertent injury to the patient.

SUMMARY

In one example, concepts presented herein relate to a delivery system having a handle. A catheter includes a lumen, a first end coupled to the handle and a second end coupled to a tip. A control module is coupled to the tip and a guidewire is coupled to the control module. The control module operates to transition between a first control state wherein the control module allows axial movement of the guidewire relative to the tip and a second control state wherein relative axial movement between the tip and guidewire is prevented.

In another example, a method includes receiving a delivery system having a proximal handle, a delivery sheath capsule and a tip maintaining a control module. The system is loaded with a radially expandable stent frame. The delivery sheath capsule contains the stent frame in a compressed arrangement over an inner shaft assembly. The prosthetic heart valve is delivered in the compressed arrangement to an implantation site using a guidewire and the control module is operated to prevent movement of the guidewire relative to the tip. The method further includes retracting the delivery sheath capsule such that the stent frame can expand to an expanded arrangement.

In yet another example, a stent frame delivery system has a handle including at least one actuator. A catheter is coupled to the actuator and includes a lumen and a delivery sheath capsule compressively retaining a stent frame and a tip positioned distal the delivery sheath capsule. A guidewire is positioned within the handle and the lumen of the catheter and a control module is coupled with the tip. The control module controls the guidewire to allow movement of the guidewire relative to the handle during a first control state and prevent movement of the guidewire relative to the handle during a second control state.

BRIEF DESCRIPTION OF THE DRAWINGS

FIG. 2 is a schematic sectional view of a handle coupled with a control module for a guidewire.

FIG. 3 is a schematic view of a proximal end of a handle coupled with a control module for a guidewire.

DETAILED DESCRIPTION

Figure 1:
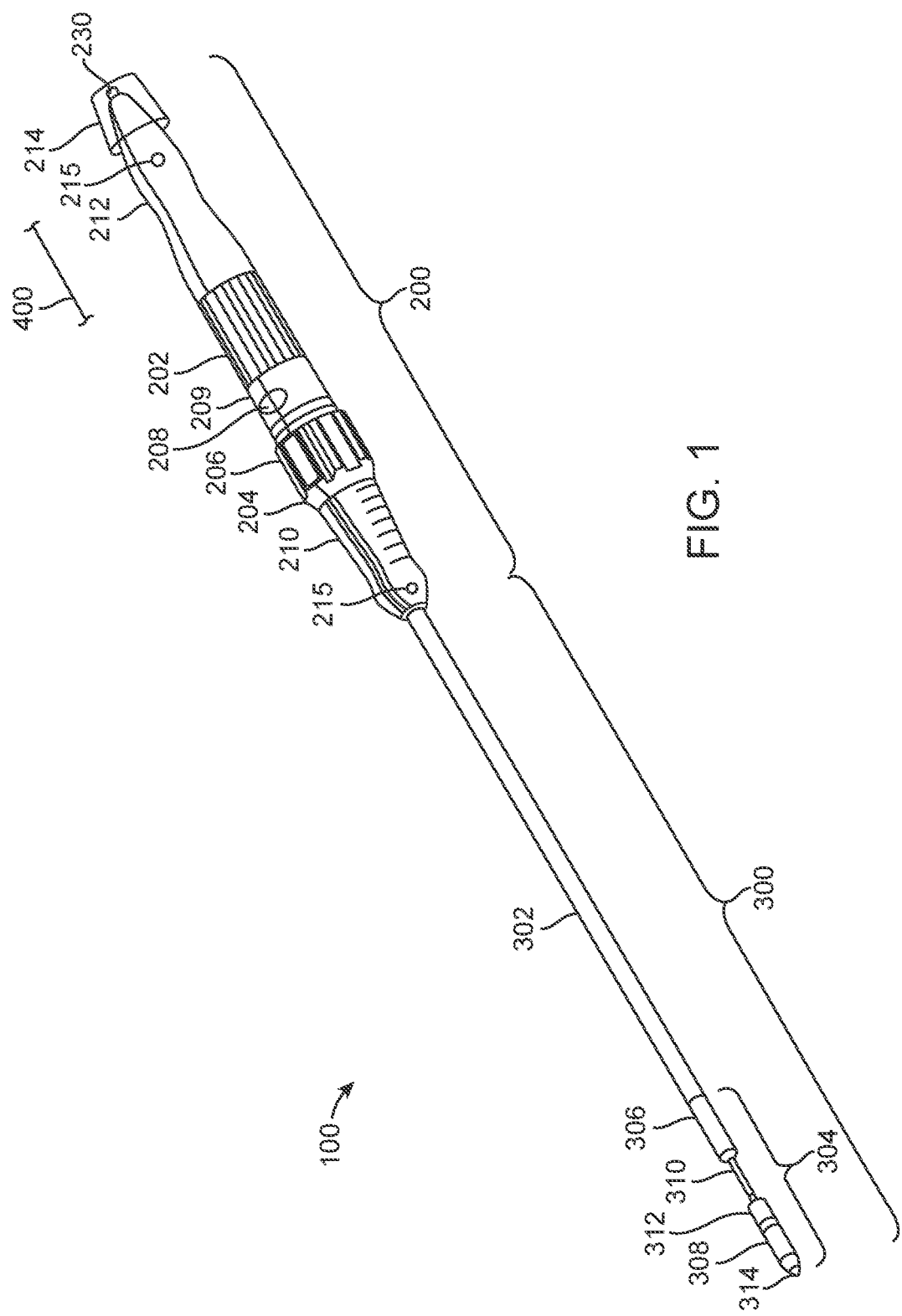
FIG. 1 is an isometric view of a delivery system employing a control module for a guidewire.

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense, and the scope of the present disclosure is defined by the appended claims. It is to be understood that features of the various examples described herein may be combined, in part or whole, with each other, unless specifically noted otherwise.

While the disclosure refers to illustrative embodiments for particular applications, it should be understood that the disclosure is not limited thereto. Modifications can be made to the embodiments described herein without departing from the spirit and scope of the present disclosure. Those skilled in the art with access to this disclosure will recognize additional modifications, applications, and embodiments within the scope of this disclosure and additional fields in which the disclosed examples could be applied. Therefore, the following detailed description is not meant to be limiting. Further, it is understood that the systems and methods described below can be implemented in many different embodiments. The operation and behavior of the systems and methods presented are described with the understanding that modifications and variations of the embodiments are possible given the level of detail presented.

References to "one embodiment," "an embodiment," "in certain embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The delivery systems disclosed herein can include a moldable handle capable of translating linear relative movement between multiple shafts simultaneously to deliver a valve prosthesis. The delivery systems can include a two-part prosthesis containment capsule which can maintain a compressible interference fit, mitigating risks associated with snagging during retraction of the delivery system. The delivery system handle can be reversibly decoupled, allowing for rapid closure of the prosthesis containment capsule after delivery of the prosthesis. The decoupling mechanism can be user operated and can include a safety feature to prevent premature actuation.

The delivery system can also include a safety stop feature on the handle, which can permit only partial deployment of one or more components of the valve prosthesis, such as valve prosthesis support arms, such as by impeding the rotation of a handle support arm knob, to allow repositioning or recapturing of the prosthesis. The user can then choose to release the safety stop button to allow the handle support arm knob to continue to be rotated until completion of the deployment of one or more components of the valve prosthesis, such as the deployment of the valve prosthesis support arms.

The delivery system can also include a delivery catheter, which can have a two-part valve prosthesis containment capsule divided into distal and proximal portions. To deploy the valve prosthesis, the proximal capsule portion can be retracted proximally to release one or more portions of the valve prosthesis. The distal capsule portion can be advanced distally to release one or more portions of the valve prosthesis. After full valve prosthesis deployment, the distal and proximal capsule portions can be returned to their closed, pre-deployment configuration to allow safe removal of the delivery system through the deployed prosthesis.

FIG. 1 illustrates an example delivery system 100, which can include a handle 200 and a catheter 300. Handle 200 can include front grip 210, rear grip 212, valve release knob 202, support arm knob 204, safety stop button 206, handle decoupling button 208, and decoupling portion 209 and guidewire control module 214. Catheter 300 can include outer shaft 302 and capsule 304. Capsule 304 can include proximal capsule portion 306, distal capsule portion 308, inner shaft 310, valve containment sleeve 312, and capsule tip 314.

Front grip 210 and rear grip 212 can be ergonomically designed to facilitate grasping of handle 200 by the user. Front grip 210 and rear grip 212 can be made of a moldable material, such as plastic or rubber, which can provide a smooth and frictional gripping surface. Front grip 210 and rear grip 212 can include grip flush ports 215, which can be used, for example, to remove air or add fluid to delivery system 100. Rear grip 212 can also include end flush port 230, which can also be used for these purposes, and additionally for inserting surgical tools through handle 200. Support arm knob 204, valve release knob 202, safety stop button 206, and handle decoupling button 208 are all features that can be used to deploy a valve prosthesis and then rejoin the capsule portions 306 and 308 after valve prosthesis deployment.

In certain embodiments, valve containment sleeve 312 can be a cylindrical polymer sleeve, configured to retain a valve prosthesis within capsule 304. In certain embodiments, capsule tip 314 can be an atraumatic tip to prevent or minimize damage to a patient's organs and vascular system as delivery system 100 is advanced through the patient's body. In certain embodiments, capsule tip 314 can include an opening at its distal end to allow delivery system 100 to pass over a guide wire. In certain embodiments, capsule tip 314 can be radiopaque to facilitate locating delivery system 100 within the body of a patient using medical imaging.

To facilitate deployment, proximal capsule portion 306 can be retracted in the proximal direction, for example, by rotating support arm knob 204, which is coupled to proximal capsule portion 306 through outer shaft 302. As such, force placed on outer shaft 302 is translated to proximal capsule portion 306. It is understood that the term support arm knob is exemplary. By support arm knob, the disclosure includes knobs, slides, switches and other similar structures that can be activated to cause proximal capsule portion 306 to move axially.

A safety stop feature can be located on handle 200, for example, within support arm knob 204, and can prevent proximal retraction of proximal capsule portion 306 beyond a predetermined distance. The safety stop feature can permit only partial deployment of the valve prosthesis support arms. Medical imaging can be used to determine the location of the support arms, and, if not in the proper location, the valve prosthesis can be repositioned or recaptured. Once in the proper deployment location, the user can activate safety stop button 206 on support arm knob 204 to allow further proximal retraction of proximal capsule portion 306. The safety stop button 206 can be a button, switch, knob, or other similar structures that can prevent proximal retraction of proximal capsule portion 306.

Distal capsule portion 308 can be advanced distally, such as by rotating valve release knob 202. It is understood that the term valve release knob is exemplary. By valve release knob, the disclosure includes knobs, slides, switches and other similar structures that can be activated to cause distal capsule portion 308 to move axially.

Valve release knob 202 can control inner shaft 310, which, in one embodiment, can be connected to distal capsule portion 308. By advancing distal capsule portion 308, and thus valve containment sleeve 312, in the distal direction, the valve prosthesis can be released.

Manual retraction of distal capsule portion 308 can be performed, for example, by rotating valve release knob 202 in a direction opposite to the direction that advances distal capsule portion 308. Manual retraction of distal capsule portion 308 can also be performed by pressing handle decoupling button 208, which can decouple decoupling portion 209 of handle 200. The user can then pull decoupling portion 209 of handle 200 proximally. This movement can pull the inner shaft 310, which can be connected to distal capsule portion 308, in the proximal direction, thus retracting distal capsule portion 308 proximally to mate with proximal capsule portion 306. Once capsule 304 is closed, delivery system 100 can be safely retracted through the deployed valve prosthesis and removed from the body.

Guidewire control module 214, in one embodiment, can be positioned at a proximal end of handle 200, adjacent rear grip 212. As discussed in more detail below, a guidewire 400 can be inserted through the handle 200 and catheter 300 to assist in delivery of the capsule 308. The control module 214 operates to transition between a first control state and a second control state. In the first control state, the control module allows relative movement between the guidewire 400 and the catheter 300. In one particular embodiment, the control module 214 axially moves the guidewire 400 relative to the catheter 300 in the first control state. In the second control state, relative movement between guidewire 400 and the catheter 300 is prevented.

In certain embodiments, the control module 214 can be coupled to rear grip 212 as illustrated in FIG. 1, or otherwise integrated into the handle 200 and/or catheter 300 as desired. To effectuate control of the guidewire, the control module 214 may include a lumen for which the guidewire can pass through. In addition, the control module 214 may include one or more mechanisms that engage the guidewire so as to perform one or more of the following: control advancement and retraction of the guidewire with respect to the handle 200 and/or the catheter 300, detect actuation of portions of the handle 200 and/or the catheter 300, detect advancement and retraction of the guidewire with respect to the handle 200 and/or the catheter 300, lock the guidewire with respect to the handle 200 and/or the catheter 300 and mechanically feed the guidewire relative to the handle 200 and/or the catheter 300.

With the above features in mind, FIG. 2 is a schematic, sectional view of a portion of one embodiment of delivery system 100. Control module 214 is secured to rear grip 212 with a press or interference fit. In other embodiments, control module 214 can be connected with a threaded interface or other mechanism as desired. Control module 214 defines a lumen 216 that receives a guidewire 400. In addition, control module 214 includes a switch 218 and a locking or clamping mechanism 220. The locking mechanism 220 as shown includes opposed jaws positioned on either side of the guidewire 400. Upon operation of switch 218, locking mechanism 220 closes, preventing further movement of guidewire 400 relative to the control module 214.

During operation, guidewire 400 is inserted through lumen 216 and through a luer lock 230 positioned at a proximal end of the handle 200. The guidewire is further inserted into a guidewire shaft seal hub 232 that includes an o-ring 234 at its distal end and into a guidewire shaft 236. Guidewire shaft 236 is coupled with inner shaft 310, which includes a lumen to receive the guidewire 400. Insertion of the guidewire 400 through the inner shaft 310 can lead to tip 314 (FIG. 1). As discussed above, movement of inner shaft 310 is controlled by knob 202. In particular, rotation of knob 202 causes an actuator 240 to move in a linear direction as indicated by arrow 242. This linear movement is translated to inner shaft 310. Likewise, movement of outer shaft 302 is controlled by knob 204. Rotation of knob 204 causes an actuator 244 to move in a linear direction as indicated by arrow 246. This linear movement is translated to outer shaft 302.

One feature of control module 214 allows automatic locking of the guidewire 400 in response to movement of either the outer shaft 302 or inner shaft 310. Operation of outer shaft 302 and inner shaft 310 is performed in deployment of the attached prosthesis. During operation of these shafts, it can be desirable to lock guidewire 400 so as to prevent inadvertent injury caused by the guidewire 400 to the patient. To this end, a first sensor 250 is coupled with actuator 240, whereas a second sensor 254 is coupled with actuator 254. Upon movement of actuator 240, sensor 250 can send a suitable signal to switch 218. In response to this signal, switch 218 can operate to close locking mechanism 220 so as to prevent further movement of guidewire 400 relative to catheter 300. In a similar manner, upon movement of actuator 244, sensor 254 can send a suitable signal to switch 218, which operates to close locking mechanism 220.

In an alternative embodiment, illustrated in FIG. 3, an alternative guidewire control module 270 includes switch 218 that operates as discussed above. In addition, control module 270 also includes a manually operated switch or actuator 272, an actuating mechanism (e.g., a motor) 274 and proximal and distal engagement mechanisms 276 and 278, respectively. Motor 274 operates the engagement mechanisms 276 and 278 to control the guidewire 400. For example, upon operation of switch 218, motor 274 can operate the engagement mechanisms 276 and 278 to lock guidewire 400 relative to the control module 270.

Motor 274 can also be utilized to advance and/or retract guidewire 400 by operating engagement mechanisms 276 and 278, for example in response to a signal from switch 272. In one embodiment, switch 272 is a toggle switch capable of providing a signal in both proximal and distal directions. Regardless of the particular structure for switch 272, engagement mechanisms 276 and 278 can control movement of guidewire 400. In one example, the engagement mechanisms 276 and 278 include opposed wheels that rotate relative to the control module 270. This rotation causes movement of the guidewire 400 relative to the control module 270 based on a direction of rotation of the wheels.

Figure 4:
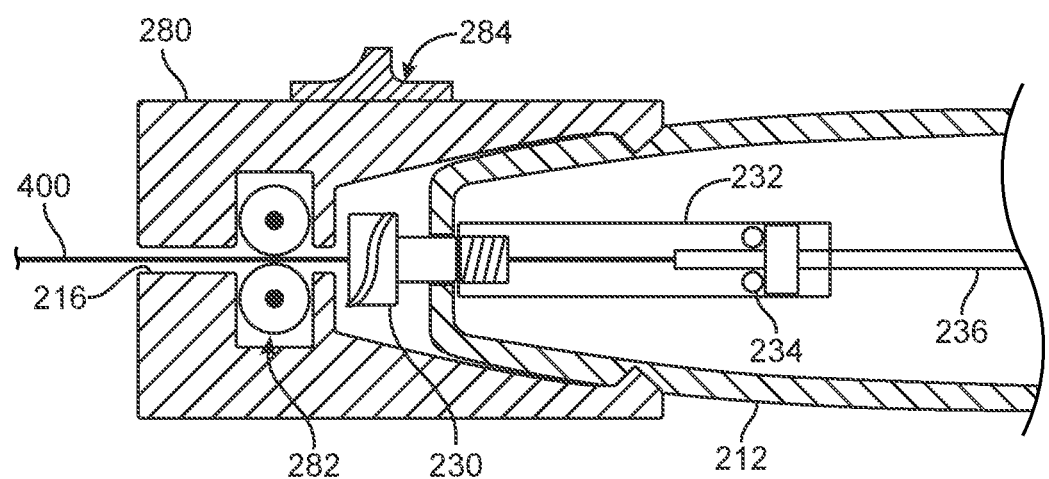
FIG. 4 is a schematic view of a proximal end of a handle coupled with a control module for a guidewire.

In yet a further embodiment, illustrated in FIG. 4, a control module 280 includes an engagement mechanism 282 and a manually operated locking switch 284. Engagement mechanism 282 can be coupled to an actuating mechanism such as a ratchet or motor to move guidewire 400 linearly with respect to the control module 280. In addition, switch 284 can be operated to lock guidewire 400 with respect to the control module 280. In one embodiment, the switch 284 is actuated so as to bias opposed wheels of engagement mechanism 282 toward one another. This actuation causes guidewire 400 to be locked with respect to control module 280. Upon release of the switch, guidewire 400 is able to be advanced and/or retracted relative to the control module 280.

In addition to control of the guidewire 400 proximate the handle 200, a distal end of the guidewire 400 can also be controlled as desired. Several embodiments are discussed below for controlling the distal end of the guidewire 400. For example, these embodiments can be operated to prevent relative movement between portions of the delivery system 100 and/or control movement of the distal end relative to portions of the delivery system 100. In specific instances, the control module allows relative movement between tip 314 of the catheter 300 and the guidewire 400 in a first control state and prevents relative axial movement between tip 314 of the catheter 300 and the guidewire 400 in a second control state. In one embodiment, the second control state provides increased strength and stiffness to the tip 314. As a result, retraction of the capsule can be performed with minimal movement of portions of the delivery system 100, providing increased accuracy for deployment of the stent frame.

Figure 5:
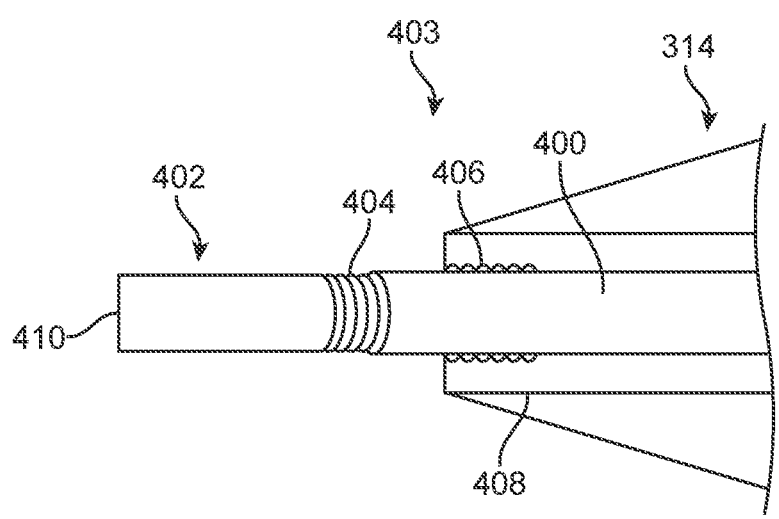
FIG. 5 is a schematic view of a control module for a guidewire coupled with a tip of a delivery system.

In one embodiment, illustrated in FIG. 5, a distal end 402 of the guidewire 400 is positioned within tip 314. A control module 403 (referenced generally) includes a first threaded section 404 and a second threaded section 406. The first threaded section 404 can mate with the second threaded section 406 on a retainer 408 or other structure. In the embodiment illustrated, the retainer 408 is coupled to capsule tip 314. During use, an operator can lock (i.e., prevent relative axial movement between the tip 314 and guidewire 400) the guidewire 400 to tip 314 (or another structure) by rotating the guidewire 400 such that threaded section 404 mates with the threaded section 406. Although illustrated as spaced apart from a distal tip 410 of the distal end 402, threaded section 404 can alternatively be located at the distal tip 410 or spaced apart therefrom at various distances.

Figure 6A:
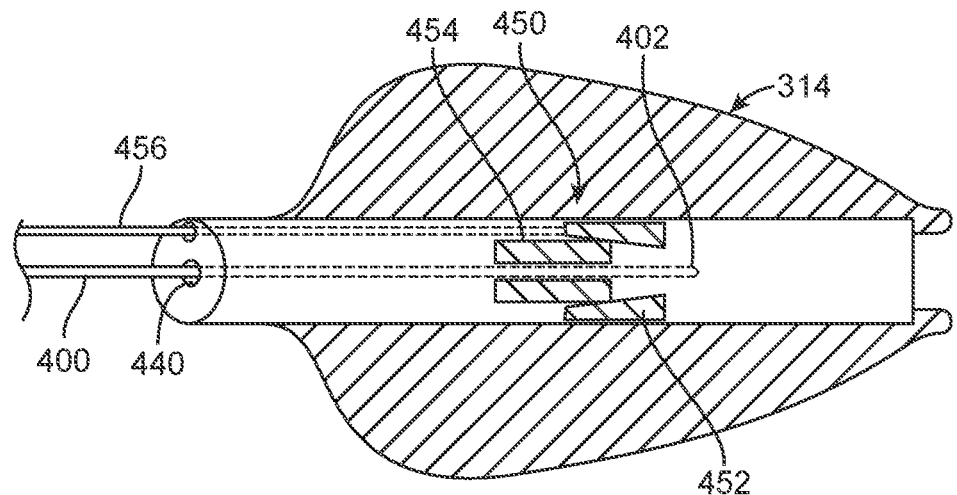
FIGS. 6A and 6B are schematic views of a control module for a guidewire coupled with a tip of a delivery system.
Figure 6B:
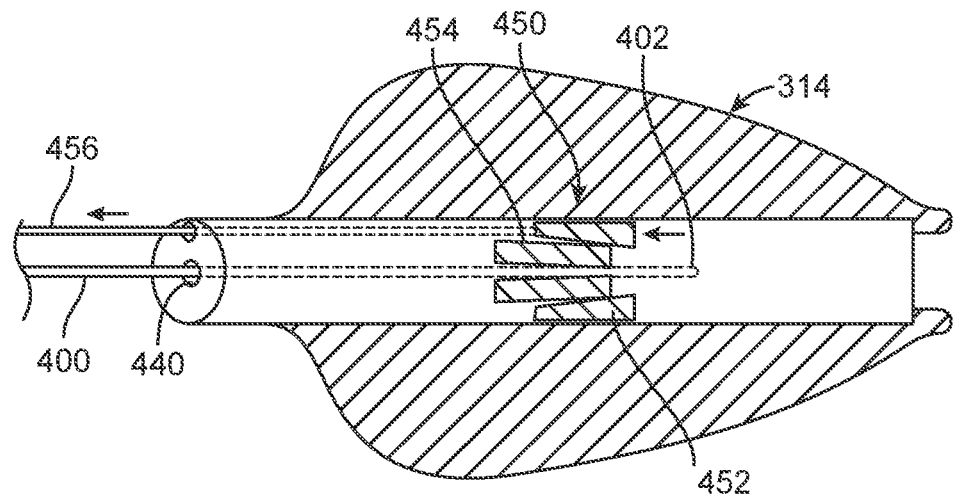

FIGS. 6A and 6B illustrate a first control state and a second control state, respectively, for an alternative embodiment to control the distal end 402 of guidewire 400. In the illustrated embodiment, the guidewire 400 is disposed within a guidewire lumen 440. The tip 314 is coupled with a guidewire control module 450 that includes a moving section 452, a stationary section 454 and a control mechanism 456. Collectively, the moving section 452 and stationary section 454 form a collet with inclined surfaces arranged such that, upon actuation of the moving section 452 relative to the stationary section 454, a force is applied to the guidewire 400 so as to prevent movement of the guidewire 400 relative to tip 314. To apply this force, the control mechanism 456 is connected with the handle 200 (not shown) and the moving section 452. A pulling force can be applied to the control mechanism in a direction away from the tip 314, causing movement of the moving section 452 relative to the stationary section 454. In the first control state of FIG. 6A, the control module 450 is spaced apart from the distal end 402 of the guidewire 400. In the second control state of FIG. 6B, after a force has been applied to control mechanism 456, the control module 450 transitions to the second control state, wherein the control module 450 is in contact with the guidewire 400 and prevents movement between the guidewire 400 and the tip 314.

Figure 7A:
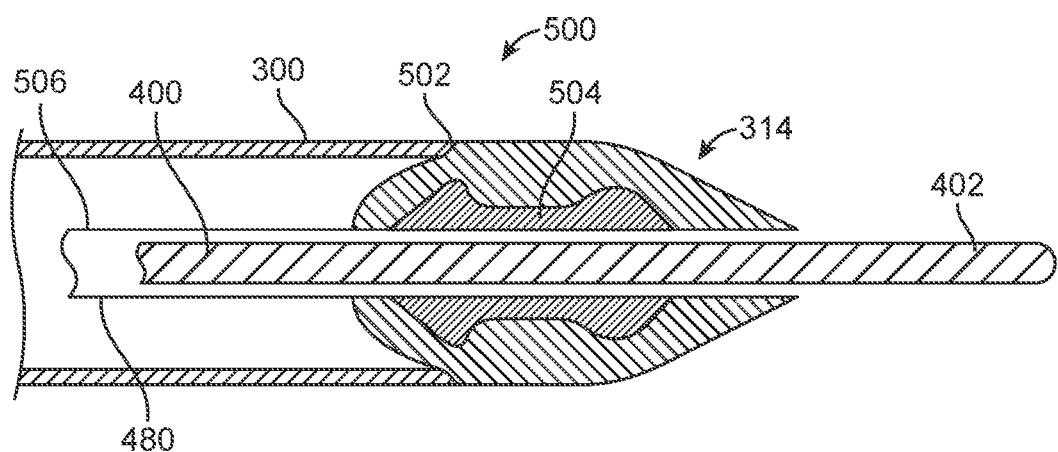
FIGS. 7A and 7B are schematic views of a control module for a guidewire coupled with a tip of a delivery system.
Figure 7B:
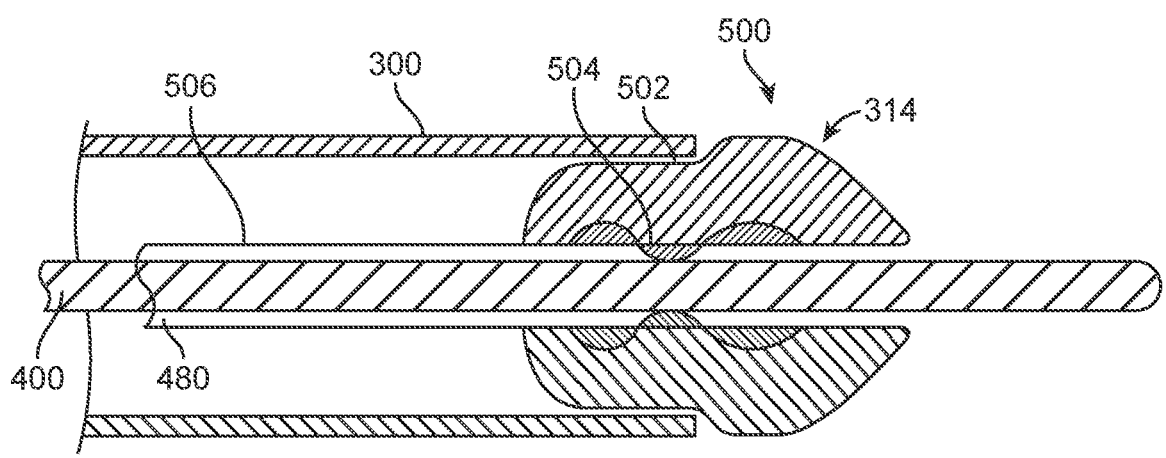

FIGS. 7A and 7B illustrate an alternative embodiment for controlling distal end 402 of guidewire 400 disposed within a guidewire lumen 480. A guidewire control module 500 (referenced generally) operates in a first control state (FIG. 7A), allowing movement between catheter 300 and guidewire 400, and a second control state (FIG. 7B), preventing movement between catheter 300 and guidewire 400. The control module 500 includes a contact surface 502, engagement member 504 and a tip control mechanism 506. In the first control state of FIG. 7A, the contact surface 502 of tip 314 is adjacent to and/or engaging catheter 300. Engagement member 504, disposed within the tip 314, is spaced apart from the guidewire 400, allowing relative movement between the catheter 300 and the guidewire 400. Upon applying a force to the tip control mechanism 506 relative to tip 314 (e.g., by pushing catheter 300 or pulling a proximal end of the tip control mechanism 506 coupled with handle 200), tip 314 is compliant so as to be forced within the catheter 300.

As illustrated in FIG. 7B, contact surface 502 compresses the tip 314 due to a size of the inner surface of the catheter 300. This compression, in turn, places force on the engagement member 504. Ultimately, the engagement member 504 contacts the guidewire 400 and transitions to the second control state where relative movement between the guidewire 400 and the catheter 300 is prevented. A variety of different mechanisms can be integrated and/or coupled with engagement member 504. For example, the engagement member 504 can include a projection or other structure to grasp the guidewire 400 so as to assist holding the guidewire 400 relative to the catheter 300. In a further embodiment, engagement member 504 can provide tactile feedback to an operator upon transitioning from the first control state of FIG. 7A to the second control state of FIG. 7B.

Figure 8A:
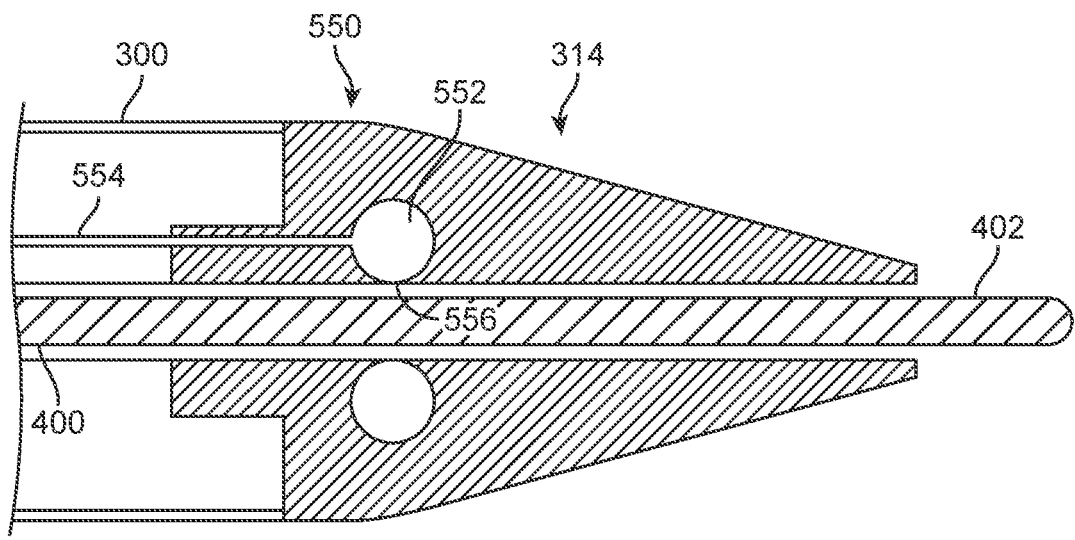
FIGS. 8A and 8B are schematic views of a control module for a guidewire coupled with a tip of a delivery system.
Figure 8B:
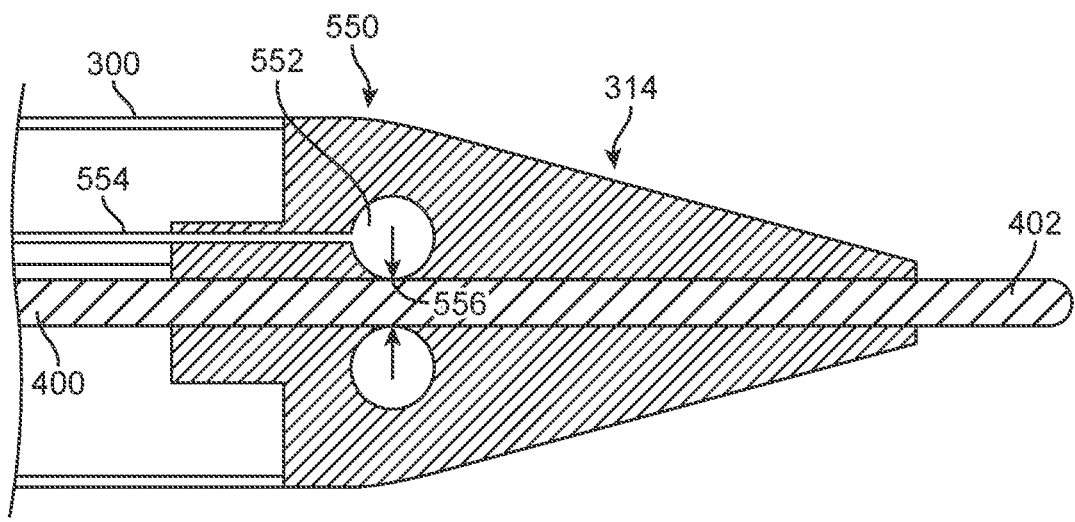

In another embodiment, illustrated in FIGS. 8A and 8B, an alternative guidewire control module 550 (referenced generally) includes an inflatable region 552 and a conduit 554 fluidly coupled with the inflatable region 552. In a first control state illustrated in FIG. 8A, a contact surface 556 of the inflatable region 552 is spaced apart from the guidewire 400, allowing relative movement between the catheter 300 and the guidewire 400. To transition the guidewire control module 550 to a second control state, fluid (e.g., air) is provided through conduit 554 to the inflatable region 552. Additional fluid within the inflatable region 552 causes the inflatable region 552 to expand, as illustrated in a second control state of FIG. 8B. Expansion of the inflatable region 552 causes contact surface 556 to engage guide wire 400. In the second control state, engagement of the contact surface 556 and guidewire 400 prevents relative movement between the catheter 300/tip 314 and the guidewire 400. In the embodiment illustrated, inflatable region 552 is embodied as a toroid, although other shapes and configurations can be utilized. For example, the inflatable region 552 need not surround an entirety of the guidewire 400 and can be positioned on a single side of the guidewire 400.

Figure 9A:
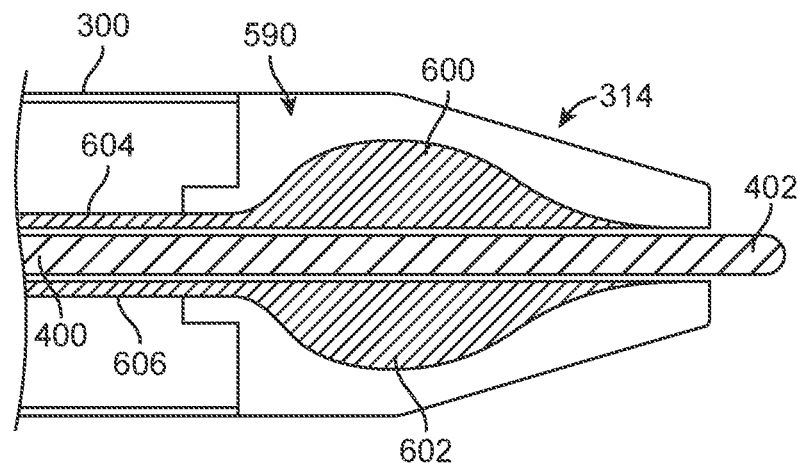
FIGS. 9A and 9B are schematic views of a control module for a guidewire coupled with a tip of a delivery system.
Figure 9B:
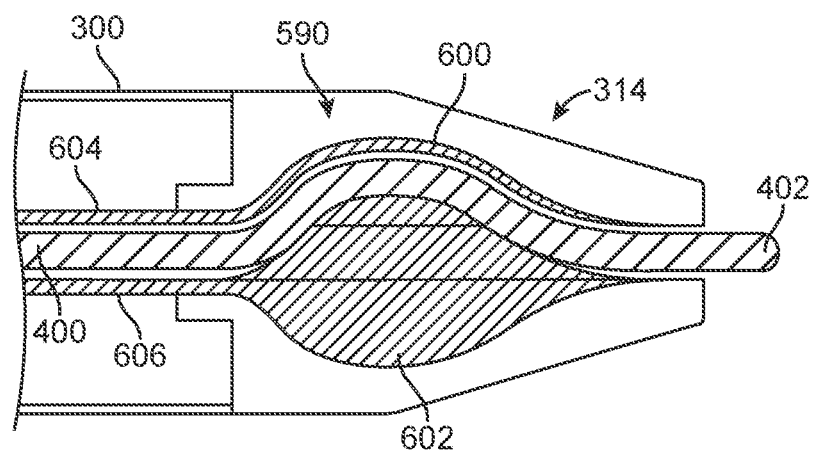

FIGS. 9A and 9B illustrate another embodiment with a guidewire control module 590 having inflatable regions 600 and 602 positioned on opposed sides of guidewire 400. Each inflatable region 600 and 602 is fluidly coupled with a corresponding conduit 604 and 606, respectively. The conduits 604, 606 are configured to provide fluid (e.g., air) to respective inflatable regions 600, 602 so as to independently inflate (i.e., increase a volume) the regions 600, 602. In a first control state of the control module 590, illustrated in FIG. 9A, the inflatable regions 600 and 602 are spaced apart from the guidewire 400, allowing relative movement between the catheter 300/tip 314 and the guidewire 400. In a second control state of the control module 590, illustrated in FIG. 9B, region 602 has been inflated, increasing its volume such that the region 602 contacts the guidewire 400 and biases that portion of the guidewire 400 toward the opposite region 600. In the second control state, relative movement between the catheter 300/tip 314 and guidewire 400 is prevented. Moreover, the guidewire 400 can be steered in a particular direction as influenced by the inflatable region 602. In one embodiment, inflation of region 602 will bias the distal end 402 of the guirewire 400 in a desired direction (e.g., angularly offset from a pushing force applied to guidewire 400). As a result, control for advancement of the guidewire 400 is achieved.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. Therefore, it is intended that this disclosure be limited only by the claims and the equivalents thereof.

The invention claimed is:

1. A delivery system, comprising:
   a guidewire; and
   a catheter assembly including:
   a catheter device defining a proximal end, a distal end opposite the proximal end, and a guidewire lumen open to the distal end and sized to receive the guidewire,
   a handle attached to the proximal end,
   an inflatable member maintained within an interior of the catheter device proximate the distal end,
   wherein the inflatable member is configured to expand from a first state to a second state;
   wherein the system is configured such that with the guidewire disposed through the guidewire lumen, the inflatable member prevents axial movement of the guidewire relative to the catheter device in the second state, and does not prevent axial movement of the guidewire relative to the catheter device in the first state, wherein the inflatable member is configured to surround less than an entirety of a circumference of the guidewire when the guidewire is disposed through the guidewire lumen.

2. The delivery system of claim 1, wherein a surface of the inflatable member is exposed to the guidewire lumen.

3. The delivery system of claim 1, wherein the system is configured such that with the guidewire disposed through the guidewire lumen, a force applied by the inflatable member onto the guidewire is greater in the second state than in the first state.

4. The delivery system of claim 1, wherein the catheter device further includes an inflation conduit fluidly open an interior of the inflatable member.

5. The delivery system of claim 4, further comprising a source of fluid connected to the inflation conduit, wherein the inflatable member transitions from the first state to the second state with delivery of fluid from the source of fluid via the inflation conduit.

6. The delivery system of claim 1, wherein the inflatable member is configured to surround a circumference of the guidewire when the guidewire is disposed through the guidewire lumen.

7. The delivery system of claim 1, wherein the catheter device defines a distal region terminating at the distal end, and further wherein an outer diameter of the distal region tapers to the distal end.

8. The delivery system of claim 7, wherein at least a portion of the inflatable member is proximal the distal region.

9. The delivery system of claim 1, wherein the system is configured such that with the guidewire disposed through the guidewire lumen, the inflatable member is spaced apart from the guidewire in the first state.

10. The delivery system of claim 1, wherein the inflatable member is a first inflatable member, and wherein the catheter assembly comprises a second inflatable member positioned opposite the first inflatable member.

11. The delivery system of claim 10, wherein the system is configured such that when the guidewire is disposed through the guidewire lumen, the first and second inflatable members are positioned on opposed sides of the guidewire.

12. The delivery system of claim 10, wherein the first inflatable member is inflatable independent of the second inflatable member.

* * * * *